(12) United States Patent
Yoo et al.

(10) Patent No.: US 8,487,999 B2
(45) Date of Patent: Jul. 16, 2013

(54) APPARATUS FOR MEASUREMENT OF SURFACE PROFILE

(75) Inventors: Young-Woong Yoo, Seoul (KR);
Young-Jin Choi, Seoul (KR);
Cheol-Hoon Cho, Yongin-si (KR)

(73) Assignee: Pemtron Co., Ltd., Seoul (KR)

( * ) Notice: Subject to any disclaimer, the term of this patent is extended or adjusted under 35 U.S.C. 154(b) by 434 days.

(21) Appl. No.: 12/598,578

(22) PCT Filed: Mar. 30, 2009

(86) PCT No.: PCT/KR2009/001611
§ 371 (c)(1),
(2), (4) Date: Jul. 30, 2010

(87) PCT Pub. No.: WO2009/142390
PCT Pub. Date: Nov. 26, 2009

(65) Prior Publication Data
US 2010/0289893 A1    Nov. 18, 2010

(30) Foreign Application Priority Data

May 19, 2008    (KR) .................. 10-2008-0046004

(51) Int. Cl.
*H04N 7/18*    (2006.01)
(52) U.S. Cl.
USPC ........................................... 348/153
(58) Field of Classification Search
USPC ................ 348/42, 46, 49, 50, 135; 356/1.6, 356/497, 601; 382/162, 164, 165
See application file for complete search history.

(56) References Cited

U.S. PATENT DOCUMENTS

| | | | |
|---|---|---|---|
| 7,466,291 B2 * | 12/2008 | Damera-Venkata et al. | ... 345/32 |
| 7,511,829 B2 * | 3/2009 | Babayoff | ...... 356/601 |
| 7,724,378 B2 * | 5/2010 | Babayoff | ...... 356/601 |
| 8,102,538 B2 * | 1/2012 | Babayoff | ...... 356/601 |
| 2005/0185192 A1 * | 8/2005 | Kim et al. | ...... 356/497 |
| 2007/0221849 A1 * | 9/2007 | Tabirian et al. | ......... 250/341.1 |
| 2008/0062290 A1 * | 3/2008 | Lahav et al. | ............. 348/280 |
| 2008/0088858 A1 * | 4/2008 | Marcu et al. | ............... 358/1.6 |
| 2011/0316978 A1 * | 12/2011 | Dillon et al. | .................. 348/46 |

* cited by examiner

*Primary Examiner* — David Czekaj
*Assistant Examiner* — Shanika Brumfield
(74) *Attorney, Agent, or Firm* — NSIP Law

(57) ABSTRACT

The present invention relates to an apparatus for measurement of the surface profile detecting 2D-image of the surface of the object. The apparatus for measurement of the surface profile according to the present invention comprises a first light source illuminating a first one-color light to the surface of the object; a second light source illuminating a second one-color light of which color is different from the first one-color light to the surface of the object; a black-and-white camera capturing the first one-color light and the second one-color light reflected from the surface of the object, which are illuminated from the first light source and the second light source; and a controller controlling the first light source, the second light source and the black-and-white camera to obtain a first black-and-white image data and a second black-and-white image data corresponding to the first one-color light and the second one-color light respectively in the state that the first one-color light and the second one-color light are illuminated to the surface of the object, and generating a synthesized color image of the surface of the object using the first black-and-white image data and the second black-and-white image data. Thus, it is possible to obtain the color 2D-image using the low-priced black-and-white camera, and it is also possible to improve processing speed by means of using the black-and-white camera of which processing speed is faster than that of a color camera.

3 Claims, 6 Drawing Sheets

(a)

(b)

APPARATUS FOR MEASUREMENT OF SURFACE PROFILE

TECHNICAL FIELD

The present invention relates to an apparatus for measurement of a surface profile, and more particularly to the apparatus for measurement of the surface profile generating a synthesized color image using a black-and-white image data obtained through a black-and-white camera.

BACKGROUND ART

As the demand for an electronic devices, such as computers, cellular phones, PDA, etc is increasing recently, an importance of a printed circuit board (PCB) using a surface mount technology (SMT) is increasing.

An apparatus for measurement of a surface profile capturing a surface profile of the PCB is used as a test device among devices composing the SMT inline system. The apparatus for measurement of the surface profile is used for detecting errors, such as a component mounting error, a soldering default, a short circuit, etc. which are occurred while the PCB is manufactured.

The apparatus for measurement of the surface profile capturing a surface profile of the PCB, installed in the SMT inline system is divided into a type of using an area-scan camera and a type of using a line-scan camera. Generally, the type of using the area-scan camera is widely used.

Meanwhile, as shown in FIG. 1, Bayer filters are attached in each pixel of a color camera used for the apparatus for measurement of surface profile, and red filters, green filters or blue filters of the Bayer filters are not adjacent to each other in each pixel.

Herein, information of three colors (R, G, and B) of each pixel is needed for making a color image using the color camera. However, one pixel of the color camera has only R or G or B information in actuality. Therefore, as shown in FIG. 2, besides one color information obtained directly from the pixel, another two color information are obtained by interpolation of the color information of adjacent pixels. FIG. 2 illustrates an example of the interpolation. The color camera is applied to a moiré system which is an apparatus for measurement of the surface profile for capturing 3D image.

Generally, 3D measurement using a moiré pattern is achieved by obtaining images while moving a grating more than 3 times at a predetermined distance in the state that the light is illuminated to the object through the grating and by detecting changes in a brightness of a measuring point. Thus, one of the key points of 3D measurement using the moiré pattern is how accurately the changes in the brightness of the measuring point or the pixel can be detected.

Generally, it is difficult to use a one-color light as a light source in 3D soldering test using the moiré pattern. For example, if a blue-color light as the light source is used for measuring red-colored surface of the PCB, the camera can't detect the light reflected from the surface of the PCB and the changes in the brightness, because a only red-color light can be reflected from surface of the PCB. Therefore, it is impossible to measure the red-colored surface of the PCB in 3D using the blue-color light as the light source.

Accordingly, a white light is used as the light source of the apparatus for measurement of the surface profile having the type of moiré 3D. However, only one of the red-color information, the green-color information and the blue-color information can be obtained from each pixel although the white light is used, the blue-color information or the green-color information is only obtained from the 66.66% pixels, with the consequence that the result of the 3D measurement cannot be relied on.

Meanwhile, the necessity of the color image is important in 2D measurement, similarly to 3D measurement as described above. Also, the color image is very important in the 2D measurement using a combined 2D and 3D measuring apparatus.

And, in case of an apparatus for the soldering test using the 2D measurement, the color image obtained by using a top lighting and a side lighting is very important for accurately discriminating the solder. However, the surface of the PCB is provided with various color. Furthermore various color contrasted with each other is painted on the surface of one PCB. Thus, the color image of which information are three times as large as that of the black-and-white image is available for discriminating the solder in 2D measurement.

Also, an inspector inspects the 2D image and the 3D image by his eyes generally and determines whether the PCB is NG or not. However, because a boundary between the solder and a pad is obscure in 2D black-and-white image, it is important that the inspector can be made to draw an accurate conclusion using 2D color image.

In spite of the importance of the color image in the apparatus for measurement of the surface profile as mentioned above, the color camera has defects, such as expensiveness and slow capture speed as compared with the black-and-white camera.

Thus, the black-and-white camera is actually and widely used in 2D or 3D apparatus for measurement of the surface profile. Also, the black-and-white camera is mainly used in the 3D measuring apparatus using the moirépattern, because a reliability of the 3D measuring result is low in spite of using the white light as described above.

However, the black-and-white camera is applied to the 3D measuring apparatus using the moiré pattern which has the type of the combined measuring apparatus available of 2D measurement with the view to the high effective value of the 3D measurement and the low cost. Accordingly, the effectiveness of the 2D measuring result is low because the boundary between the solder and the pad is obscure in the 2D black-and-white image in the 2D measurement, with the consequence that the effectiveness the 3D measuring apparatus using the moiré pattern as the 2D and 3D combined measuring apparatus is low.

DISCLOSURE

Technical Problem

The present invention has been made in view of the above problems, and it is an object of the present invention to provide an apparatus for measurement of the surface profile generating a synthesized color image using a black-and-white image data obtained through a black-and-white camera.

Technical Solution

In accordance with an aspect of the present invention, the above objects can be accomplished by the provision of an apparatus for measurement of the surface profile capturing 2D-image of a surface of an object comprising a first light source illuminating a first one-color light to the surface of the object; a second light source illuminating a second one-color light of which color is different from the first one-color light to the surface of the object; a black-and-white camera capturing the first one-color light and the second one-color light reflected from the surface of the object, which are illuminated from the first light source and the second light source; and a controller controlling the first light source, the second light source and the black-and-white camera to obtain a first black-and-white image data and a second black-and-white image data corresponding to the first one-color light and the second one-color light respectively in the state that the first one-color light and the second one-color light are illuminated to the surface of the object, and generating a synthesized color image of the surface of the object using the first black-and-white image data and the second black-and-white image data.

Here, the first one-color light comprises one of a green-color light and a blue-color light; and wherein the second one-color light comprises a red-color light.

Also, the controller calculates a third black-and-white image data corresponding to one of the green-color light and the blue-color light on the basis of the first black-and-white image data obtained by the illumination of the other of the green-color light and the blue-color light and of the second black-and-white image date, and generates the synthesized color image by synthesizing the first black-and-white image data, the second black-and-white image data and the third black-and-white image data.

And, the controller calculates the third black-and-white image data using a formula of $I\_3rd\_data = n \times (I\_1st\_data)^k + m \times (I\_2nd\_data)^p$ (here, $I\_1st\_data$ is the first black-and-white image data, $I\_2nd\_data$ is the second black-and-white image data, $I\_3rd\_data$ is the third black-and-white image data, n and k is a constant number given to the first black-and-white image data for calculating the third black-and-white image data, and m and p is a constant number given to the second black-and-white image data for calculating the third black-and-white image data).

In accordance with another aspect of the present invention, there is provided an apparatus for measurement of the surface profile capturing 2D-image of a surface of an object comprising a first light source illuminating a first one-color light to the surface of the object; a second light source illuminating a second one-color light of which color is different from the first one-color light to the surface of the object; a third light source illuminating a third one-color light of which color is different from the first one-color light and the second one-color light to the surface of the object; a black-and-white camera capturing the first one-color light, the second one-color light and the third one-color light reflected from the surface of the object, which are illuminated from the first light source, the second light source and the third light source; and a controller controlling the first source of light, the second light source, the third light source and the black-and-white camera to obtain a first black-and-white image data, a second black-and-white image data and a third black-and-white image data corresponding to the first one-color light, the second one-color light and the third one-color light respectively in the state that the first one-color light, the second one-color light and the third one-color light are illuminated to the surface of the object, and generating a synthesized color image of the surface of the object using the first black-and-white image data, the second black-and-white image data and the third black-and-white image data.

Here, the first one-color light comprises a blue-color light; the second one-color light comprises a red-color light; and the third one-color light comprises a green-color light.

Also, the controller generates the synthesized color image by means of recognizing the first black-and-white image data, the second black-and-white image data and the third black-and-white image data as RGB data of each pixel.

And, the black-and-white camera is provided with a type of an area-scan camera or a line-scan camera.

Advantageous Effects

According to the present invention, the present invention provides an apparatus for measurement of the surface profile generating a synthesized color image using a black-and-white image data obtained through a black-and-white camera. Therefore, it is possible to obtain 2D color image using the black-and-white camera which is inexpensive, and to improve processing speed by means of using the black-and-white camera of which a capture speed is higher than that of the color camera.

Also, if the present invention is applied to the 2D/3D test apparatus using the moiré pattern, efficiency of the 2D/3D test apparatus can be more improved, because the color image can be obtained in 2D measurement even though the black-and-white camera is used.

BEST MODE

The present invention relates to an apparatus for measurement of the surface profile detecting 2D-image of a surface of an object comprising a first light source illuminating a first one-color light to the surface of the object; a second light source illuminating a second one-color light of which color is different from the first one-color light to the surface of the object; a black-and-white camera capturing the first one-color light and the second one-color light reflected from the surface of the object, which are illuminated from the first light source and the second light source; and a controller controlling the first light source, the second light source and the black-and-white camera to obtain a first black-and-white image data and a second black-and-white image data corresponding to the first one-color light and the second one-color light respectively in the state that the first one-color light and the second one-color light are illuminated to the surface of the object, and generating a synthesized color image of the surface of the object using the first black-and-white image data and the second black-and-white image data

MODE FOR INVENTION OR DETAILED DESCRIPTION

Now, the present invention will be described in detail with reference to the annexed drawings.

Figure 1:
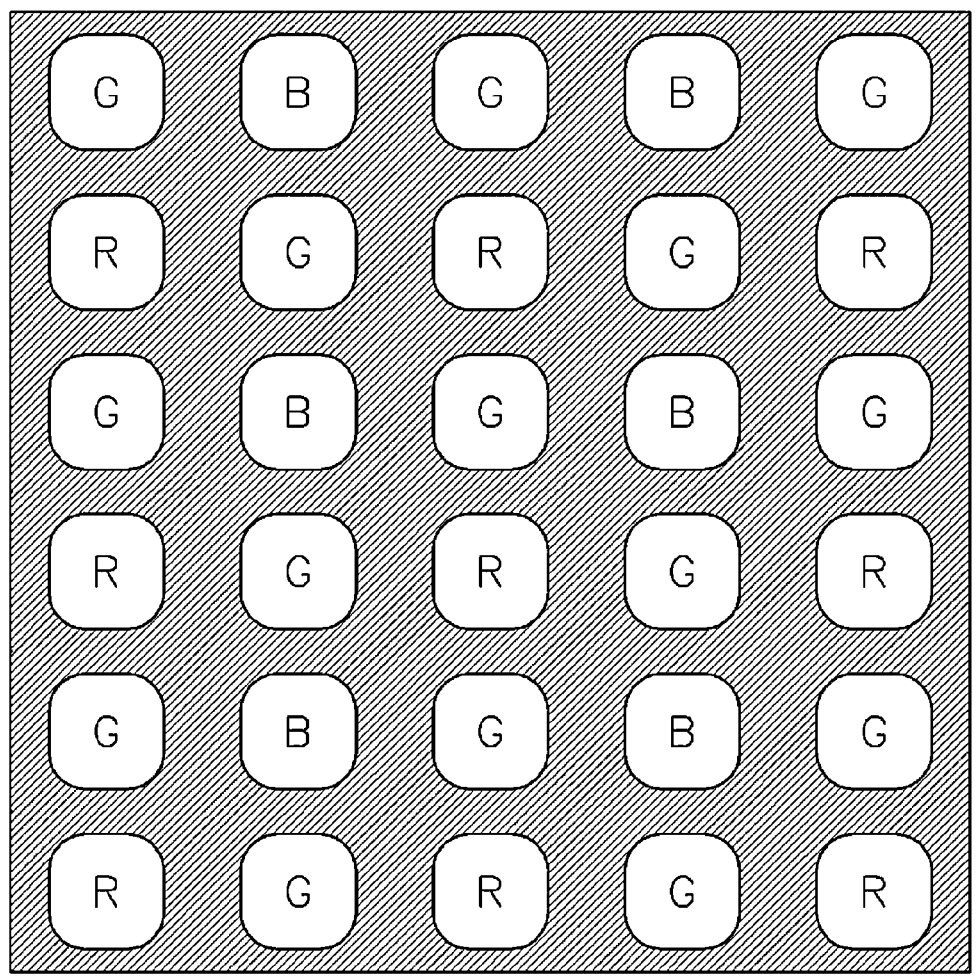
FIG. 1 and FIG. 2 are views of describing a color filter used in the color camera and a method for interpolation thereof.
Figure 2:
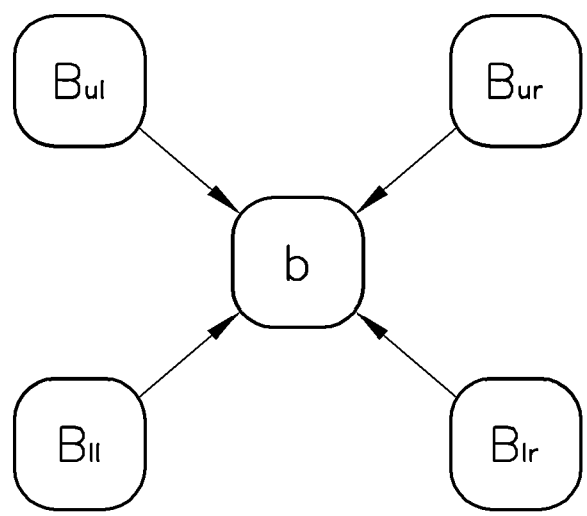
Figure 3:
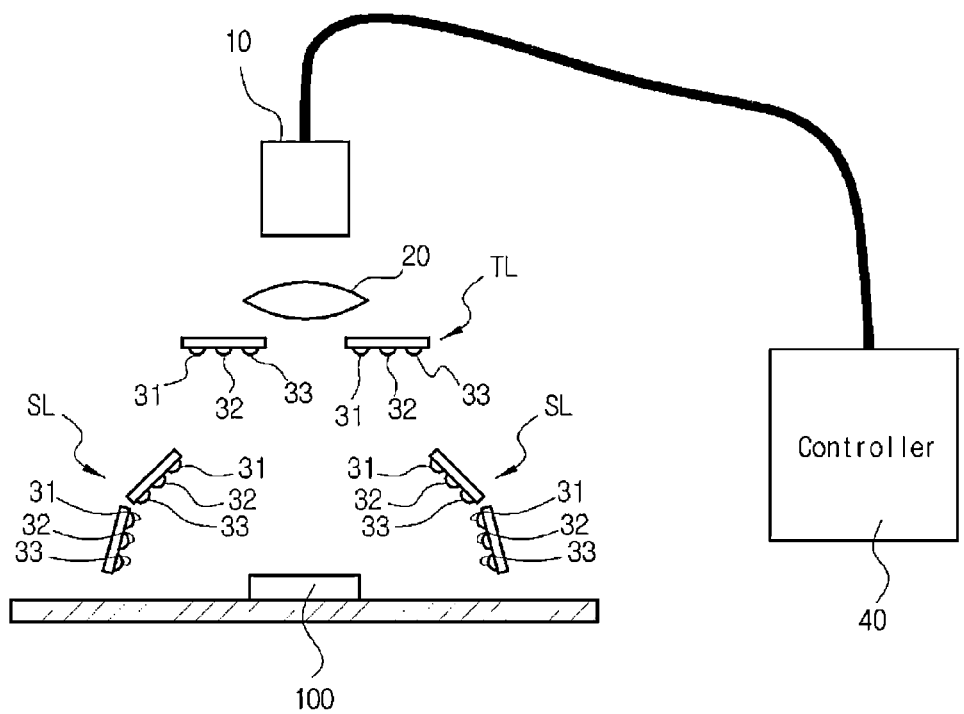
FIG. 3 illustrates an example of a constitution of an apparatus for measurement of the surface profile according to a first embodiment of the present invention.

FIG. 3 illustrates an example of a constitution of an apparatus for measurement of the surface profile according to a first embodiment of the present invention. The apparatus for measurement of the surface profile according to the first embodiment of the present invention is applied to a 2D measuring apparatus as an example.

As shown in FIG. 3, the apparatus for measurement of the surface profile according to the present invention comprises a first light source 31, a second light source 32, a black-and-white camera 10 and a controller 40.

The first light source 31 illuminates a first one-color light to the surface of the object 100, and the second light source 32 illuminates a second one-color light of which color is different from the first one-color light 31 to the surface of the object 100. Here, the first one-color light illuminated from the first light source 31 of the apparatus for measurement of the surface profile according to the present invention is a green-color light or a blue-color light as an example, and the second one-color light illuminated from the second light source 32 of the apparatus for measurement of the surface profile according to the present invention is a red-color light as an example.

And, the first light source 31 and the second light source 32 are provided with a type of a top lighting TL and/or a side lighting SL. In FIG. 3, the first light source 31 and the second light source 32 is provided with both type of the top lighting TL and the side lighting SL as an example. That is, the first light source 31 and the second light source 32 is provided with the type of the top lighting TL respectively, and the first light source 31 and the second light source 32 is provided with the type of the side lighting SL respectively as an example in the present invention. Thus, it is possible to use either the top lighting TL or the side lighting SL appropriately, or to use both the top lighting TL and the side lighting SL in accordance with the type of the object 100.

Here, the first light source 31 and the second light source 32 according to the present invention is provided with the type of a light emitting diode (LED) turned on and off according to control by the controller 40, as an example. Here, the turning on and off the LED is synchronized with the capturing of the black-and-white camera 10 according to control by the controller 40, as an example.

The black-and-white camera 10 captures the first one-color light and the second one-color light reflected from the surface of the object 100, which are illuminated from the first light source 31 and the second light source 32. And, the black-and-white camera 10 transmits a black-and-white image data obtained by capturing the first one-color light and the second one-color light to controller 40.

Hereinafter, the black-and-white image data captured and obtained by the black-and-white camera 10 in the state that the first one-color light is illuminated from the first light source 31 is defined as a first black-and-white image data. And, the black-and-white image captured and obtained by the black-and-white camera 10 in the state that the second one-color light is illuminated from the second light source 32 is defined as a second black-and-white image data.

The controller 40 controls the first light 31 and the black-and-white camera 10 to obtain the first black-and-white image data corresponding to the first one-color light in the state that the first one-color light is illuminated to the surface of the object 100. Also, The controller 40 controls the second light source 32 and the black-and-white camera 10 to obtain the second black-and-white image data corresponding to the second one-color light in the state that the second one-color light is illuminated to the surface of the object 100.

Here, the black-and-white camera 10 according to the present invention is provided with a type of an area-scan camera or a line-scan camera. And, in case that the black-and-white camera 10 is provided with the type of the area-scan camera, the controller 40 obtains the first black-and-white image data in the state that the first one-color light is illuminated from the first light source 31 when one field of view (FOV) is captured, and obtains the second black-and-white image data in the state that the second one-color light is illuminated from the second light source 32 for the same FOV. And the controller 40 can obtain the first black-and-white image data and the second black-and-white image data for the whole surface of object 100 by means of obtaining the first black-and-white image data and the second black-and-white image data for the next FOV in the same way.

Also, in case that the black-and-white camera 10 according to the present invention is provided with the type of the line-scan camera, the controller 40 can obtain the first black-and-white image data and the second black-and-white image data for the whole surface of object 100 by means of obtaining the first black-and-white image data and the second black-and-white image data for one step of a line scan.

The controller 40 obtains the first black-and-white image data and the second black-and-white image data according to the method as mentioned above, and then generates a synthesized color image for the surface of the object 100 using the first black-and-white image data and the second black-and-white image data.

Hereinafter, a method how the controller 40 generates the synthesized color is described in case that the first one-color light is the blue-color light, and the second one-color light is the red-color light as an example.

The first black-and-white image data is a data captured by the black-and-white camera 10 in the state that the blue-color light is illuminated to the surface of object 100, and the second black-and-white image data is a data captured by the black-and-white camera 10 in the state that the red-color light be illuminated to the surface of object 100.

Here, the controller 40 recognizes the first black-and-white image data as a blue data, and recognizes the second black-and-white image data as a red data among R, G, B data for generating the synthesized color image.

And, the controller 40 calculates a third black-and-white image data which is a green data among R, G, B data on the basis of the first black-and-white image data and the second black-and-white image data. Here, the third black-and-white image data is calculated using the following [Formula 1], as an example.

$$I\_3rd\_data = n \times (I\_1st\_data)^k + m \times (I\_2nd\_data)^p \quad \text{[Formula 1]}$$

Here, I_1st_data is the first black-and-white image data, I_2nd_data is the second black-and-white image data, I_3rd_data is the third black-and-white image data, n and k is a constant number given to the first black-and-white image data for calculating the third black-and-white image data, and m and p is a constant number given to the second black-and-white image data for calculating the third black-and-white image data.

The third black-and-white image data for all pixels is calculated as mentioned above, and then the controller 40 generates the synthesized color image by means of synthesizing the first black-and-white image data, the second black-and-white image data and the third black-and-white image data. At this time, the controller 40 generates the synthesized color image by means of recognizing the first black-and-white image data, the second black-and-white image data and the third black-and-white image data as R, G, B data of each pixel.

Figure 4:
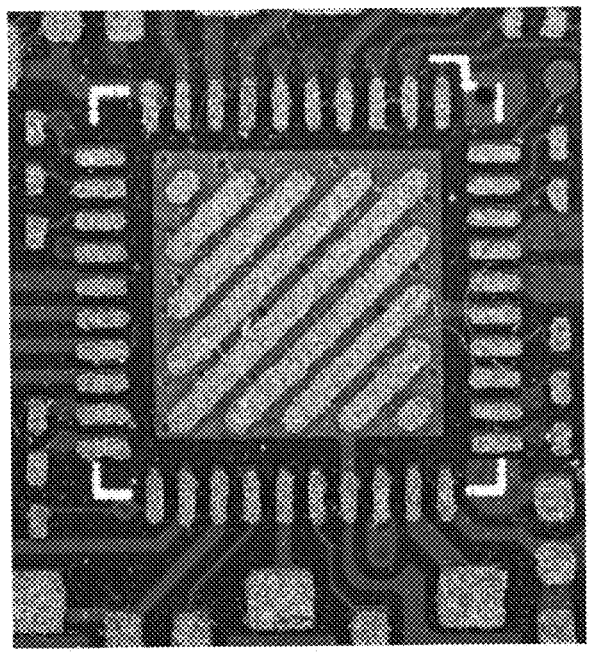
FIG. 4 illustrates examples of an 2D black-and-white image expressed by a first black-and-white image data and a second black-and-white image data obtained by the apparatus for measurement of the surface profile according to the first embodiment of the present invention.
Figure 4:
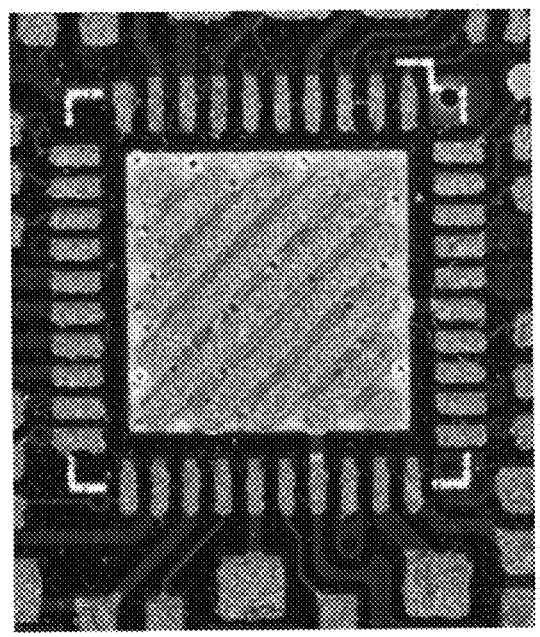
Figure 5:
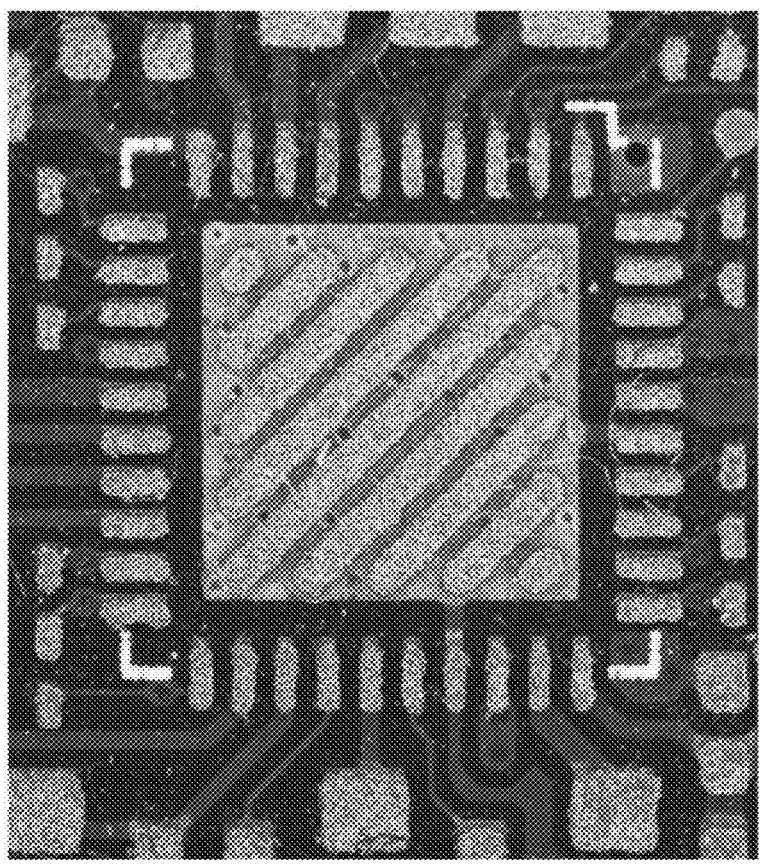
FIG. 5 illustrates an example of a synthesized color image generated using the first black-and-white image data and the second black-and-white image data in FIG. 4.

FIG. 4 and FIG. 5 illustrate examples of the first black-and-white image data and the second black-and-white image data obtained using the apparatus for measurement of the surface profile according to the present invention and the synthesized color image generated using the first black-and-white image data and the second black-and-white image data.

FIG. 4 (a) show the first black-and-white image data captured and obtained by the black-and-white camera 10 in the state that the blue-color light as the first one-color light is illuminated from the first light source 31 in black-and-white image, and FIG. 4 (b) show the second black-and-white image data captured and obtained by the black-and-white camera 10 in the state that the red-color light as the second one-color light is illuminated from the second light source 32 in black-and-white image.

As shown in FIGS. 4 (a) and (b), when the first black-and-white image data and the second black-and-white image data are obtained through the black-and-white camera 10 in the state that the first one-color light and the second one-color light are illuminated respectively, the first black-and-white image data and the second black-and-white image data have not information about color but information about brightness.

Here, If the controller 40 calculates the third black-and-white image data using the first black-and-white image data and the second black-and-white image data through the [Formula 1] and synthesizes the first black-and-white image data, the second black-and-white image data and the third black-and-white image data, and then the synthesized color image is generated as shown in FIG. 5.

As shown in FIG. 4 and FIG. 5, it is perceived that a distinction between the solder and the pad is not clear in the black-and-white image obtained by means of illuminating the blue-color light or the red-color light, whereas a distinction between the solder and the pad is clear in the synthesized color image.

Through the constitution as described above, it is possible to obtain the color image by means of generating the synthesized color image using the black-and-white image data obtained through the black-and-white camera 10 which is inexpensive, and to improve processing speed by means of using the black-and-white camera 10 of which capture speed is higher than that of a color camera.

Figure 6:
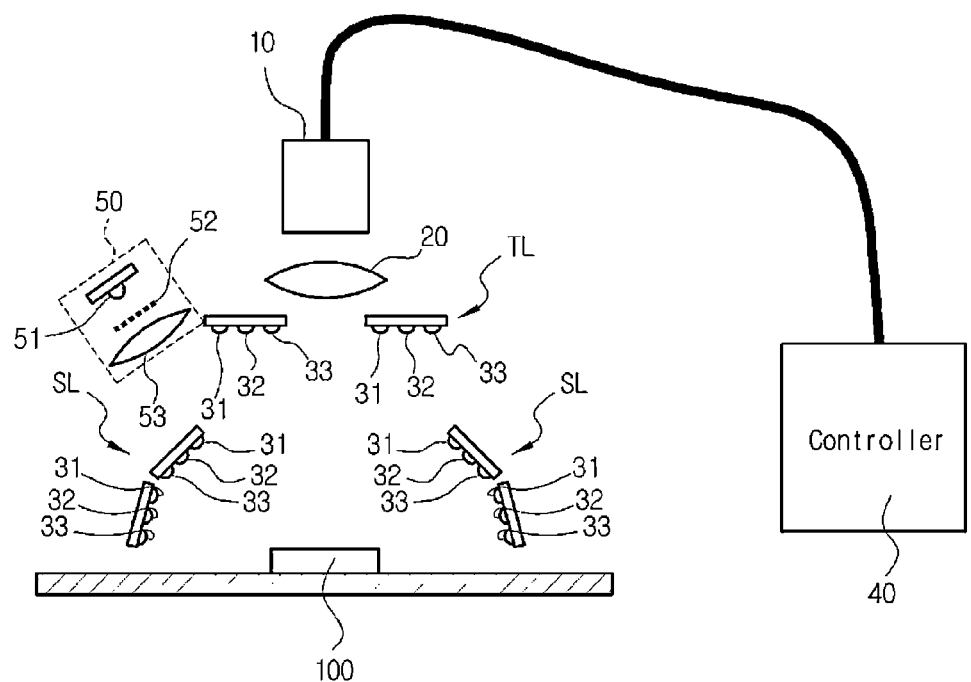
FIG. 6 illustrates an example of a constitution of an apparatus for measurement of the surface profile according to a second embodiment of the present invention.

FIG. 6 illustrates an example of a constitution of an apparatus for measurement of the surface profile according to a second embodiment of the present invention. The apparatus for measurement of the surface profile according to the second embodiment of the present invention is applied to a moiré system which is a 2D/3D measuring apparatus as an example.

As shown in FIG. 6, the apparatus for measurement of the surface profile according to the second embodiment of the present invention comprises a 3D light source part 50, a black-and-white camera 10, a first light source 31, a second light source 32 and a controller 40.

The 3D light source part 50 illuminates light to the surface of the object 100 in case of 3D measuring. Here, The 3D light source part 50 according to the present invention comprises a 3D light source 51 placed at a predetermined intervals from a reference plate (not shown, of which surface is equal to the surface of the PCB ideally in case that the object 100 is the PCB) on which the object 100 is placed, and a projection grid 52 formed a grid pattern and placed between the object 100 and the 3D light source 51

It is preferable to use a light source illuminating a white light as 3D light source 51, and a laser diode which is small, lightweight, cheap comparatively and called as a semiconductor laser, or a halogen light source or LED light source can be used. And, a projection lens 53 projecting the light passing through the projection grid 52 to the object 100 may be placed between the projection grid 52 and the object 100 and be adjacent to the projection grid 52.

The grid pattern is formed on the projection grid 52. The light illuminated from the 3D light source 51 is converted into a grid patterned light by passing through the projection grid 52. And, 3D information about the surface of the object 100 can be obtained by a moiré pattern which is formed by reflection of the grid patterned light from the surface of the object 100.

Here, the projection grid 52 is moved microscopically in the horizontal direction to the direction of light transmission by a grid moving part (not shown). Accordingly, a phase shift of the grid pattern formed on the projection grid 52 is available, and then the controller 40 obtains the 3D information about the surface of the object 100 by means of the moirépattern passed through the projection grid 52, reflected from the surface of the object 100 and captured by the black-and-white camera 10.

Meanwhile, obtainment of a 2D image by the apparatus for measurement of the surface profile illustrated in FIG. 6 is corresponding to the above-mentioned first embodiment. That is, the controller 40 controls the first light source 31 and the black-and-white camera 10 to obtain the first black-and-white image data corresponding to the first one-color light in the state that the first one-color light is illuminated to the surface of the object 100. Also, The controller 40 controls the second light source 32 and the black-and-white camera 10 to obtain the second black-and-white image data corresponding to the second one-color light in the state that the second one-color light is illuminated to the surface of the object 100.

And, the first black-and-white image data and the second black-and-white image data are obtained, and then the controller 40 generates the synthesized color image for the surface of the object 100 using the first black-and-white image data and the second black-and-white image data.

Here, the process that the controller 40 calculates the third black-and-white image data using the first black-and-white image data and the second black-and-white image data and generates the synthesized color image for the surface of the object 100 using the first black-and-white image data, the second black-and-white image data and the third black-and-white image data is equal to that of the above-mentioned first embodiment.

In this manner, by means of obtaining the color image in case of 2D measurement and obtaining the 3D black-and-white image without the loss of the color information caused by obtaining the color image in case of 3D measurement, in spite of installing the black-and-white camera 10 in the 2D/3D measuring apparatus using the moiré pattern, it is possible to enhance the efficiency of 2D/3D measuring apparatus.

In the above-mentioned embodiments, the first black-and-white image data and the second black-and-white image data is obtained through the black-and-white camera 10. And, the third black-and-white image data is calculated using the first black-and-white image data and the second black-and-white image data, as an example.

Whereas, the apparatus for measurement of the surface profile according to the present invention may comprise a third light source 33 illuminating a third one-color light of which color is different from the first one-color light and the second one-color light to the surface of the object 100. And the controller 40 may obtain a third black-and-white image data by means of controlling the black-and-white camera 10 to capture a image for the surface of the object 100 in the state that the third one-color light is illuminated to the surface of the object 10.

Accordingly, the controller 40 obtains the first black-and-white image data, the second black-and-white image data and the third black-and-white image data corresponding to the first one-color light, the second one-color light and the third one-color light through the black-and-white camera 10, generates the synthesized color image by means of recognizing the first black-and-white image data, the second black-and-white image data and the third black-and-white image data as R, G, B data.

Meanwhile, a reference number 20 in FIGS. 3 and 6 which is not described above is a condensing lens condensing the light reflected from the object 100 to a direction toward the black-and-white camera 10.

Also, in the above-mentioned second embodiment of the present invention, the apparatus for measurement of the surface profile for 2D/3D measurement uses moiré technology, as an example. In addition, the apparatus for measurement of the surface profile according to the present invention may be applied to a 3D measuring apparatus of which type is different from that of moiré technology in case of 2D measurement.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents

INDUSTRIAL APPLICABILITY

The present invention is applicable to a field of measurement of the surface profile generating a synthesized color image using a black-and-white image data obtained through a black-and-white camera.

The invention claimed is:

1. An apparatus for measurement of a surface profile capturing 2D-image of a surface of an object, the apparatus comprising;
   a first light source illuminating a first one-color light to the surface of the object;
   a second light source illuminating a second one-color light of which color is different from the first one-color light to the surface of the object;
   a black-and-white camera capturing the first one-color light and the second one-color light reflected from the surface of the object, which are illuminated from the first light source and the second light source; and
   a controller controlling the first light source, the second light source and the black-and-white camera to obtain a first black-and-white image data and a second black-and-white image data corresponding to the first one-color light and the second one-color light respectively in the state that the first one-color light and the second one-color light are illuminated to the surface of the object, and generating a synthesized color image of the surface of the object using the first black-and-white image data and the second black-and-white image data
   wherein the first one-color light comprises one of a green-color light and a blue-color light, and the second one-color light comprises a red-color light,
   the controller calculates a third black-and-white image data corresponding to one of the green-color light and the blue-color light on the basis of the first black-and-white image data obtained by the illumination of the other of the green-color light and the blue-color light and of the second black-and-white image data, and generates the synthesized color image by synthesizing the first black-and-white image data, the second black-and-white image data and the third black-and-white image data, and
   the controller calculates the third black-and-white image data using a formula of I_3rd_data=n×(I_1st_data)$^k$+ m×(I_2nd_data)$^p$ (here, I_1st_data is the first black-and-white image data, I_2nd_data is the second black-and-white image data, I_3rd_data is the third black-and-white image data, n and k is a constant number given to the first black-and-white image data for calculating the third black-and-white image data, and m and p is a constant number given to the second black-and-white image data for calculating the third black-and-white image data).

2. The apparatus for measurement of the surface profile according to claim 1, wherein the controller generates the synthesized color image by means of recognizing the first black-and-white image data, the second black-and-white image data and the third black-and-white image data as RGB data of each pixel.

3. The apparatus for measurement of the surface profile according to claim 1, wherein the black-and-white camera is provided with a type of an area-scan camera or a line-scan camera.

* * * * *